US011921048B2

United States Patent
Jeong et al.

(10) Patent No.: US 11,921,048 B2
(45) Date of Patent: Mar. 5, 2024

(54) NANOCOMPOSITE NANOSTRUCTURE-BASED SURFACE-ENHANCED RAMAN SCATTERING RESPIRATORY DROPLET MASK SENSOR AND FABRICATION METHOD THEREFOR

(71) Applicant: Korea Advanced Institute of Science and Technology, Daejeon (KR)

(72) Inventors: Ki-Hun Jeong, Daejeon (KR); Charles Soon Hong Hwang, Daejeon (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 0 days.

(21) Appl. No.: 18/050,551

(22) Filed: Oct. 28, 2022

(65) Prior Publication Data

US 2024/0019376 A1    Jan. 18, 2024

(30) Foreign Application Priority Data

Jul. 13, 2022  (KR) .......................... 10-2022-0086534

(51) Int. Cl.
 *G01N 21/65*    (2006.01)
(52) U.S. Cl.
 CPC .................................. *G01N 21/658* (2013.01)
(58) Field of Classification Search
 CPC ............... G01N 21/658; Y10S 977/855; Y10S 977/707; Y10S 977/953
 See application file for complete search history.

(56) References Cited

U.S. PATENT DOCUMENTS

| | | | |
|---|---|---|---|
| 2012/0287427 A1* | 11/2012 | Li .......................... | B82Y 20/00 977/773 |
| 2013/0242297 A1* | 9/2013 | Thoniyot ............... | B82Y 40/00 356/244 |
| 2019/0310200 A1* | 10/2019 | Lee ...................... | G01N 21/658 |
| 2019/0331605 A1* | 10/2019 | Park .......................... | G01J 3/44 |
| 2022/0192537 A1* | 6/2022 | Milner ................... | G06N 20/00 |

* cited by examiner

*Primary Examiner* — Roy M Punnoose
(74) *Attorney, Agent, or Firm* — McDonnell Boehnen Hulbert & Berghoff LLP

(57) ABSTRACT

The present disclosure relates to a fine particle-trapping sensor including: a plasmonic hotspot layer formed of a first metal; and a trapping layer formed of a second material. The inventors of the present disclosure have made extensive research efforts to develop a more effective and novel sensor for the real-time and high-sensitivity detection of droplets emitted from the oral cavity. As a result, the inventors have developed an alloy composite nanostructure including a Raman sensor layer, formed of a metal, and a trapping layer formed of a dielectric material, and have found that, when the ratio between the two layers is adjusted, the alloy composite nanostructure effectively traps respiratory droplets rapidly emitted from the oral cavity and detects coronavirus (SARS-CoV-2 lysate) in the respiratory droplets at a concentration of 10 pfu/ml, indicating that the composite nanostructure may be very advantageously used in the field of fine particle trapping.

20 Claims, 8 Drawing Sheets

FIG. 4

NANOCOMPOSITE NANOSTRUCTURE-BASED SURFACE-ENHANCED RAMAN SCATTERING RESPIRATORY DROPLET MASK SENSOR AND FABRICATION METHOD THEREFOR

CROSS-REFERENCE TO RELATED APPLICATIONS

This application claims the benefit of priority of Korean Patent Application no. KR-10-2022-0086534, filed Jul. 13, 2022, which is hereby incorporated herein by reference in its entirety.

BACKGROUND

1. Technical Field

The present disclosure relates to an alloy composite nanostructure-based surface- enhanced Raman scattering respiratory droplet mask sensor and a method for fabricating the same.

2. Related Art

Respiratory particulates generated in the human body exist in the form of gaseous volatile organic compounds (VOCs) and in the form of respiratory aerosols (droplets). In recent years, studies have been conducted on the early diagnosis of various diseases, including diabetes, gastric cancer, lung cancer, dementia, and the like, by detection of various biomarkers present in the respiratory particulates. In particular, due to the recent spread of coronavirus, interest in respiratory droplets has increased.

Representative methods of detecting droplets include physical impaction, evaporative light scattering detection, and Raman and surface-enhanced Raman scattering (SERS). Thereamong, the physical impaction method is a method of sorting droplets according to their size and then individually examining the sorted droplets, and is capable of analyzing the components of droplets, but has disadvantages in that it is difficult to quantitatively analyze droplets, and for a biological sample, a culturing process is required, which takes a time period of up to about two weeks. The evaporative light scattering detection (ELSD) method is a method of analyzing components based on scattering angle and scattering wavelength by evaporating aerosol droplets and irradiating the aerosol droplets with light, and is capable of quantitative analysis at 100 ng level, but has limitations in that an expensive system is used and a measurement time of 1 hour or more is required. On the other hand, the aerosol detection method based on the Raman and surface-enhanced Raman scattering (SERS) technique has advantages in that it is capable of detection even at a single-molecule level and capable of real-time measurement, and thus it has recently attracted a lot of attention. In recent years, studies have been conducted to determine the level of air pollution using the SERS technique by collecting droplets in the air. However, there are limitations in detecting respiratory droplets using the SERS technique. The first limitation is the difference in sample volume. In a conventional SERS technique, about 1 μL of a sample is dropped on a SERS substrate and subjected to measurement, but respiratory droplets have an average volume of 1 pL, and thus it is difficult to ensure the same volume of respiratory droplets on the same area of the SERS substrate. The second limitation is the low surface energy of the conventional SERS substrate due to the geometric feature thereof. Specifically, the conventional SERS substrate is fabricated to have a high packing density in order to increase the number of plasmonic hotspots, and thus the average contact angle thereof is 75° or more, and for this reason, a problem arises in that the wettability of the substrate naturally decreases. Respiratory droplets in the human body are emitted at a speed of about 2 to 10 m/s on average, and when they come into contact with a surface having low surface energy, they are not successfully adsorbed onto the surface, but are rebounded from the surface.

Therefore, the inventors of the present disclosure have conducted studies to develop a more effective and novel sensor for the real-time and high-sensitivity detection of droplets. As a result, the present inventors have developed an alloy composite nanostructure including a Raman sensor layer, formed of a metal, and a trapping layer formed of a dielectric material, and have found that, when the ratio between the two layers is adjusted, the alloy composite nanostructure effectively traps respiratory droplets rapidly emitted from the oral cavity and detects coronavirus (SARS-CoV-2 lysate) in the respiratory droplets at a concentration of 10 pfu/ml. The present disclosure is expected to be very widely used for detection of droplets emitted from the oral cavity.

SUMMARY

The inventors of the present disclosure have made extensive research efforts to develop a more effective and novel sensor for the real-time and high-sensitivity detection of droplets emitted from the oral cavity. As a result, the present inventors have developed an alloy composite nanostructure including a Raman sensor layer, formed of a metal, and a trapping layer formed of a dielectric material, and have found that, when the ratio between the two layers is adjusted, the alloy composite nanostructure effectively traps respiratory droplets rapidly emitted from the oral cavity and detects coronavirus (SARS-CoV-2 lysate) in the respiratory droplets at a concentration of 10 pfu/ml, thereby completing the present disclosure.

Therefore, an object of the present disclosure is to provide a fine particle-trapping sensor including: a plasmonic hotspot layer formed of a first metal; and a trapping layer formed of a second material.

However, objects to be achieved by the present disclosure are not limited to the above-mentioned object, and other objects not mentioned herein will be clearly understood by those of ordinary skill in the art from the following description.

Hereinafter, various embodiments described herein will be described with reference to figures. In the following description, numerous specific details are set forth, such as specific configurations, compositions, and processes, etc., in order to provide a thorough understanding of the present disclosure. However, certain embodiments may be practiced without one or more of these specific details, or in combination with other known methods and configurations. In other instances, known processes and preparation techniques have not been described in particular detail in order to not unnecessarily obscure the present disclosure. Reference throughout this specification to "one embodiment" or "an embodiment" means that a particular feature, configuration, composition, or characteristic described in connection with the embodiment is included in at least one embodiment of the present disclosure. Thus, the appearances of the phrase "in one embodiment" or "an embodiment" in various places throughout this specification are not necessarily referring to the same embodiment of the present disclosure. Additionally, the particular features, configurations, compositions, or characteristics may be combined in any suitable manner in one or more embodiments.

Unless otherwise stated in the specification, all the scientific and technical terms used in the specification have the same meanings as commonly understood by those skilled in the technical field to which the present disclosure pertains.

Throughout the present specification, it is to be understood that when any part is referred to as "including" any component, it does not exclude other components, but may further include other components, unless otherwise specified.

According to one aspect of the present disclosure, the present disclosure provides a fine particle-trapping sensor including: a plasmonic hotspot layer formed of a first metal; and a trapping layer formed of a second material.

The inventors of the present disclosure have made extensive research efforts to develop a more effective and novel sensor for the real-time and high-sensitivity detection of droplets emitted from the oral cavity. As a result, the present inventors have developed an alloy composite nanostructure including a Raman sensor layer, formed of a metal, and a trapping layer formed of a dielectric material, and have found that, when the ratio between the two layers is adjusted, the alloy composite nanostructure effectively traps respiratory droplets rapidly emitted from the oral cavity and detects coronavirus (SARS-CoV-2 lysate) in the respiratory droplets at a concentration of 10 pfu/ml.

As used herein, the term "metal" generally refers to a material that is hard and glossy shiny and has high thermal and electrical conductivities. In chemistry, the term "metal" is used as an expression referring to both transition metals and post-transition metals, but metalloids are sometimes included in the definition of metals. In general, metal exists in a solid state at room temperature, has a characteristic luster, acts as a conductor that transmits heat and electricity well, and has ductility and malleability. About three-quarters of the 118 elements located on the periodic table fall within the general definition of metals. Iron, copper, aluminum, gold, tin, uranium, etc. are commonly found in nature. In general, metallic elements tend to lose electrons and become positive ions, whereas non-metals tend to gain electrons.

As used herein, the term "plasmonic" refers to generating, sensing and manipulating signals at optical frequencies along metal-dielectric interfaces at the nanometer scale.

According to a specific embodiment of the present disclosure, the sensor is an alloy composite nanostructure.

As used herein, the term "alloy" refers to a material having metallic properties obtained by combining a metal with another metal or element. The alloy has properties different from those of the original metal.

As used herein, the term "nanostructure" may be classified according to material into inorganic nanostructures, organic nanostructures, polymer inorganic nanostructures, porous high-surface-area nanostructures, and bio-related nanostructures. The inorganic nanostructures are structures attracting attention in relation to mainly semiconductors, and are related to studies in the fields of quantum structures, single electronic elements, next-generation memory elements, and magnetic recording media. The organic nanostructure field includes fullerene, carbon nanotubes, carbon nanofibers, diamond thin films, organic EL, and the like. The polymer inorganic nanostructures may be typically identified in two fields, including nanostructure-controlling polymers and ceramic nanoparticles. The porous high surface area nanostructures include activated carbon fibers, zeolites and photocatalytic particles. The bio-related nanostructures include drug delivery systems, biomimetic elements, high-sensitivity nanosensor materials, and the like. The single-electron effects in nanostructures are mainly observed in junctions or quantum dots having tunnel barriers. If the size of the junction is large, the linear characteristic is measured by measuring the current-voltage curve.

As used herein, the term "sensor" refers to an element and device that collect information on a certain object and convert the information to a signal that may be handled by a machine. Humans act based on information obtained through sight, hearing, taste, smell, touch, and the like, but machines also perform control and processing based on information obtained from sensors.

According to a specific embodiment of the present disclosure, the sensor is a sensor capable of continuously trapping fine particles.

According to a specific embodiment of the present disclosure, the sensor is a sensor capable of binding to any one or more selected from the group consisting of silicone, silicon oxide, silicon nitride, paper, and fiber.

As used herein, the term "silicone" refers to a polymer based on a framework of alternating silicon and oxygen bonds. When dichlorodimethylsilane synthesized by allowing methyl chloride ($CH_3Cl$) to react with crystalline silicon is hydrolyzed, a siloxane bond is formed. Several types of polymers are possible depending on a polymerization method. A typical example of the silicone is a silicone resin composed of linear polydimethylsiloxane and oligosiloxane molecules.

As used herein, the term "silicon nitride ($Si_3N_4$)" refers to a ceramic in which nitrogen and silicon are bonded to have a composition of $Si_3N_4$. The silicon nitride is a material widely used as a heat-resistant ceramic. $Si_3N_4$ is the most thermodynamically stable and commercially important material among silicon nitrides. It is a relatively chemically inert white high-melting-point solid that is etched by dilute hydrogen fluoride (HF) and hot phosphoric acid $H_3PO_4$).

As used herein, the term "fiber" refers to a natural or artificial material whose length is significantly longer than the width. Natural fibers have a shape elongated in a certain direction due to changes in cells or protoplasm contained in cells.

According to a specific embodiment of the present disclosure, the sensor is a layered nanostructure.

According to a specific embodiment of the present disclosure, the first metal is any one or an alloy of two or more selected from the group consisting of gold (Au), silver (Ag), copper (Cu), aluminum (Al), lead (Pb), and palladium (Pd).

As used herein, the term "gold" refers to a chemical element having a symbol of Au and an atomic number of 79. Gold is a shiny yellow, brittle transition metal that is ductile and malleable. It does not chemically react with other chemicals, but reacts with chlorine, fluorine, and aqua regia. It occurs as lump metal or as grains of rock or alluvial earth.

As used herein, the term "silver" is a chemical element having a symbol of Ag and an atomic number of 47. Silver is a soft, white, shiny transition metal that has superior electrical and thermal conductivity compared to other metals. Silver is produced in the form of silver ore or pure silver, and is used for coins, ornaments, tableware, photographs, silver medals, and the like.

As used herein, the term "copper" is a chemical element having a symbol of Cu and an atomic number of 29. Copper is a soft metal having very high thermal and electrical conductivities, and the surface of copper shows a pinkishorange color before contact with air. Copper is mainly used as a medium for transferring heat or electricity, and is also used as a raw material for building materials or various alloys. Copper is one of the rare metals that exist in a pure form that can be used immediately without smelting among metal elements that exist in nature due to its relatively low reactivity. Copper is a naturally occurring rare metal that exists in a pure form and may be used immediately without smelting due to its relatively low reactivity.

As used herein, the term "aluminum" refers to a chemical element belonging to the post-transition metal family and having a symbol of Al and an atomic number of 13. Aluminum is a silvery-white, soft metal, is rich in malleability and ductility, and may be made into a foil or wire. Commercially available aluminum has a purity of 98.0 to 99.85%, and the main impurities thereof are silicon and iron. The properties of aluminum depend on the purity. Aluminum is a good conductor of electricity, and the resistivity thereof is about 1.6 times that of copper. In addition, aluminum is a typical light metal in terms of specific gravity.

As used herein, the term "lead" refers to a chemical element having a symbol of Pb and an atomic number of 82. Lead is a soft, heavy, malleable and toxic post-transition metal, and the cross-section thereof is bluish, but discolors in air to a dull gray color. Lead is an element having the largest atomic number among the stable elements. Lead has a low melting point, so it is easy to solder, causes lead poisoning, and has good absorption ability. It is also contained in paint ingredients. It is the last element in nature with stable isotopes that do not undergo radioactive decay.

As used herein, the term "palladium" refers to a chemical element having a symbol of Pd and an atomic number of 46. Palladium is a silvery-white rare element belonging to the transition metal family. It belongs to the platinum group element, has chemical properties similar to those of platinum, and is extracted from copper or nickel ores. It is mainly used as a catalyst and ornaments. It was discovered by the British chemist William Hyde Wollaston in 1803 and named after the asteroid Pallas. Among platinum group elements including platinum, rhodium, ruthenium, iridium, palladium, osmium, and the like, palladium has the lowest melting point and density.

According to a specific embodiment of the present disclosure, the second material is a metal oxide. More specifically, the second material is any one or an alloy of two or more selected from the group consisting of titanium dioxide ($TiO_2$), zinc oxide (ZnO), nickel oxide (NiO), and stannous oxide (SnO).

As used herein, the term "titanium dioxide" is also called titanium dioxide or titanium dioxide, and the chemical formula of titanium dioxide is $TiO_2$. Titanium dioxide is a molecule in which one titanium atom as a transition metal and two oxygen atoms are bonded. It has a molecular weight of 79.866 g/mol, and is tasteless, odorless white powder. When titanium is exposed to air, it readily reacts with oxygen to form a titanium dioxide layer. It has very high oxidizing power, is insoluble in almost all solvents due to its high hiding power, exhibits anisotropy with a very high refractive index anisotropy, and also has high scattering ability. In addition, it is a very stable non-toxic material.

As used herein, the term "zinc oxide" refers to an inorganic compound having a chemical formula of ZnO. ZnO is white powder that does not dissolve in water, and is used as an additive in various materials and products such as cosmetics, food supplements, rubber, plastics, ceramics, glass, cement, lubricants, paints, ointments, adhesives, sealants, pigments, food, batteries, ferrites, or flame retardants.

As used herein, the term "nickel oxide (NiO)" refers to a compound having a formula of NiO. Nickel oxide is used in the fabrication of nickel alloys, including nickel steel alloys and the fabrication of glass and porcelain paints, is a major component of a nickel-iron battery or nickel-cadmium rechargeable battery, and is used to make frits and porcelain glazes in the ceramic industry. It also serves as a hydrogenation catalyst, and nickel oxide/carbon nanotubes (NiO/CNTs) may be a potential cathode catalyst for oxygen reduction reaction (ORR) in microbial fuel cells (MFCs).

As used herein, the term "stannous oxide (SnO)" refers to a compound having the formula SnO. Stannous tin is composed of tin having an oxidation state of +2 and oxygen, and there are two forms of stannous oxide: a stable blue-black form, and a metastable red form.

According to a specific embodiment of the present disclosure, the trapping layer is formed by depositing the second material, followed by self-assembled monolayer coating.

As used herein, the term "self-assembled monolayer" refers to a high-dimensional molecular assembly in which functional molecules are arranged laterally by chemical adsorption on the surface.

According to a specific embodiment of the present disclosure, the second material has a higher surface energy than the first metal.

As used herein, the term "surface energy" is an important concept needed to understand a thin layer, and refers to extra energy to expand a surface. In general, metals have high surface energy, and oxide layers have low surface energy. Surface energy is important in determining the degree of wetting of one material by another material or in forming a uniform adhesion layer. A material having a low surface energy tends to wet a material having a high surface energy, whereas a material having a high surface energy forms a cluster or a droplet on a material having a low surface energy. When the surface energy of water is higher than the surface energy of a thin layer, hydrophobicity appears, and when the surface energy of water is lower, hydrophilicity appears.

According to a specific embodiment of the present disclosure, the trapping layer is located on the surface of the plasmonic hotspot layer.

According to a specific embodiment of the present disclosure, the trapping layer is located in the form of a cluster on the surface of the plasmonic hotspot layer.

According to a specific embodiment of the present disclosure, the fine particle is a particulate matter, pollen, fungus, heavy metal, or droplet.

As used herein, the term "particulate matter (PM)" refers to a fine particle having a very small particle size so as to be invisible to the naked eye. Particulate matter is an air pollutant containing sulfur dioxide, nitrogen oxide, lead, nitrogen dioxide, ozone, carbon monoxide, or the like. It is a fine particle having a particle diameter of 10 µm or less, which is generated in automobiles, factories, cooking processes, etc. and floats in the air for a long period of time. It is also referred to as PM 10. A particulate matter having a particle size of 2.5 µm or less is referred to as PM 2.5 and is also called "ultra-fine particulate matter"' or "very fine particulate matter". Scientifically, it is called an aerosol droplet. Fine particles are also called suspended particles, particulate matter, or the like, and have slightly different meanings depending on their names. Particulate matter has a diameter of about 10 nm to 100 µm, and if the diameter is larger than the upper limit of the above range, the residence time in the atmosphere is very short due to gravity.

As used herein, the term "fungus" refers to a microscopic fungus that grows in a group that can be identified under suitable conditions. Fungi are ubiquitous both indoors and outdoors year-round.

As used herein, the term "heavy metal" refers to any metal having a specific gravity of 45 or more. In general, when the heavy metal binds to an in vivo substance to form an organic complex that is not easily degraded. Thus, the heavy metal has a strong property of accumulating in parenchymal organs, such as the liver and kidneys, or bones, without being quickly emitted out of the body.

As used herein, the term "respiratory droplet" is also referred to as a droplet, and refers to a particle which falls to the ground after being emitted, is composed mostly of water, and has a diameter greater than 5 μm. Respiratory droplets may be produced naturally as a result of breathing, speaking, sneezing, coughing, or vomiting, or may also be produced artificially through aerogel-generating medical procedures, toilets, or other household activities.

According to another aspect of the present disclosure, the present disclosure provides a method for fabricating a fine particle-trapping sensor, the method including steps of: (a) forming a plasmonic hotspot layer of a first metal; and (b) forming a trapping layer of a second material.

According to a specific embodiment of the present disclosure, the first metal in step (a) is any one or an alloy of two or more selected from the group consisting of gold (Au), silver (Ag), copper (Cu), aluminum (Al), lead (Pd), and palladium (Pd).

According to a specific embodiment of the present disclosure, the second material in step (b) is any one or an alloy of two or more selected from the group consisting of titanium dioxide ($TiO_2$), zinc oxide (ZnO), nickel oxide (NiO), and stannous oxide (SnO).

According to a specific embodiment of the present disclosure, the surface energy is determined by contact angle measurement.

As used herein, the term "contact angle" refers to an angle of an interface formed when a liquid comes into contact with an immiscible material. It is known that the contact angle between a liquid and a solid, especially in a gas or vacuum state, forms the thermodynamic equilibrium of surface energy between the gas, liquid and solid.

According to still another aspect of the present disclosure, the present disclosure provides a method for fine particle component analysis, the method including steps of: (a)—trapping fine particles by the above-described fine particle-trapping sensor; (b) measuring a surface-enhanced Raman spectroscopy (SERS) signal from the fine particles; and (c) analyzing the SERS signal by a machine learning-based algorithm.

As used herein, the term "surface-enhanced Raman spectroscopy (SERS)" refers to a surface-sensitive technique that enhances Raman scattering by molecules or nanostructures such as plasmonic magnetic silica nanotubes, adsorbed on a rough metal surface, and means a high-sensitivity analytical technique that obtains information on a material by adsorbing the material onto a nano-sized metal surface and amplifying a Raman scattering signal, which is difficult to detect due to its weak signal intensity. The enhancement factor may range from 1,010 to 1,011, and this technique is capable of detecting single molecules.

According to the present disclosure, Raman scattering is a phenomenon in which kinetic energy increases or decreases when light interacts with molecules and photons are scattered differently depending on molecular identity. Scattering is a phenomenon in which a portion of light travels in a direction different from the traveling direction when the light passes through a certain medium. Raman scattering refers to a phenomenon in which, when a sample (liquid or solid) is irradiated with monochromatic light, slightly different light is created in the flux of scattered light, thus changing the wavelength of the light. Raman scattering was discovered by the Indian scientist Chandrasekhara Venkata Raman in 1928 and named after him. Surface-enhanced Raman scattering utilizes a plasmonic phenomenon which is a unique optical property of the surface of a nano-metal nanostructure. That is, when the surface of a metal nanostructure having a size smaller than a wavelength is irradiated with light, an electromagnetic field caused by surface plasmon, the enhancement of the Raman scattering signal occurs through the amplification of an electromagnetic field by surface plasmon, which is the phenomenon of collective vibration of electrons, which is caused by the interaction between light and electrons at the boundary between the metal surface and the dielectric. The shape of the surface of the metal nanostructure affects the amplification of the electric field, thereby affecting the capability to detect molecular vibrations on the SERS-active surface, and the capability is quantified by the quantity called enhancement factor.

As used herein, the term "machine learning" refers to the study of computer algorithms that automatically improve through experience. The machine learning is a field of artificial intelligence that develops algorithms and technologies that enable computers to learn.

According to a specific embodiment of the present disclosure, the algorithm is one or more selected from the group consisting of autoencoding, logistic regression, principal component analysis, and confusion matrix.

As used herein, the term "autoencoder" refers to an unsupervised learning technique that converts an input into a signal by an encoder and then creates a label by a decoder.

As used herein, the term "logistic regression" refers to a statistical technique that is used to predict the probability of occurrence of an event using a linear combination of independent variables. The purpose of logistic regression is to express the relationship between the dependent variable and the independent variable as a specific function and use the function in a future predictive model, similar to the goal of general regression analysis. Logistic regression is similar to linear regression analysis in that it explains the dependent variable as a linear combination of the independent variables. However, unlike linear regression analysis, logistic regression may be regarded as a kind of classification technique because the dependent variable targets categorical data and the results of the corresponding data are divided into specific classifications when input data is given.

As used herein, the term "principal component analysis (PCA)" refers to a technique that reduces high-dimensional data to low-dimensional data. In this case, orthogonal transformation is used to transform samples in a high-dimensional space, which are likely to be correlated with each other, into samples in a low-dimensional space, which have no linear correlation. When data are mapped to one axis, the data are linearly transformed into a new coordinate system such that the axis with the largest variance is placed as the first principal component and the axis with the second largest variance as the second principal component. This decomposition of sample differences into the components that best represent them provides several benefits for data analysis.

As used herein, the term "confusion matrix" generally refers to a specific table layout that may visualize the performance of a supervised learning algorithm. Unsupervised learning is generally referred to as an agreement matrix. Each row of the matrix represents the instances in an actual class while each column represents the instances in a predicted class, or vice versa.

According to a specific embodiment of the present disclosure, the algorithm is capable of identifying multiple target constituents.

According to a specific embodiment of the present disclosure, the fine particle is a particulate matter, pollen, fungus, heavy metal, or droplet.

The present disclosure is directed to an alloy composite nanostructure-based respiratory droplet mask sensor capable of effectively trapping respiratory droplets by an alloy composite nanostructure Raman substrate and performing quantitative analysis by Raman signal measurement based on machine learning, and a method for fabricating the same.

According to the present disclosure, it is possible to effectively trap respiratory droplets, rapidly emitted from the oral cavity, through surface energy optimization, and to obtain a high-efficiency Raman signal by a Raman sensor layer having high nanostructure packing density and a large number of plasmonic hotspots. In addition, it is possible to separate and measure signals of various targets present in respiratory droplets by machine learning-based Raman signal processing.

According to the present disclosure, the alloy composite nanostructure is composed of a plasmonic hotspot layer and a trapping layer. In an example of the present disclosure, the plasmonic hotspot layer was formed of gold (Au) nanoislands, and the trapping layer was formed of $TiO_2$. As a result, it could be confirmed that the surface energy of the alloy composite nanostructure SERS substrate changed depending on whether the trapping layer was deposited, as a result of measuring the contact angle.

According to the present disclosure, R6G aerosol was sprayed through a nebulizer and the SERS signal was measured in order to analyze the properties of the alloy composite nanostructure SERS substrate, and it was confirmed that the SERS signal was significantly enhanced at a specific alloy ratio (thickness of the trapping layer). In addition, it was confirmed that, as the thickness of the trapping layer increased, the surface energy of the substrate increased, so that more droplets were adsorbed, but the plasmonic hotspots were inhibited, resulting in a decrease in the signal intensity. In addition, optimization of the alloy ratio was performed, and it was confirmed that the result is consistent with the theory that the SERS signal decreases to the cube of the distance. Specifically, it was confirmed that the contact angle increased as the thickness of the trapping layer ($TiO_2$) increased. More specifically, it was confirmed that, when the thickness was 2 nm, it was possible to measure the SERS signal with the highest intensity for R6G aerosol, and as the ($TiO_2$) thickness further increased, the measurement of the SERS signal for R6G aerosol decreased. Accordingly, a critical value of the thickness was determined.

According to the present disclosure, the alloy composite nanostructure has a two-layered nanostructure, and the metal layer, which is the first layer of the alloy composite nanostructure, is formed of a material including any one selected from the group consisting of Au, Ag, Cu, Al, Pb, and Pd. Among the above-mentioned metals, an alloy of two or more different metals may also be used. The metal layer of the present disclosure has a thickness of 10 nm to 100 nm, and the size of the individual nanostructure is 20 nm to 200 nm. The metal layer of the present disclosure may be formed by a process such as photolithography, soft lithography, or solid-phase dewetting, without being limited thereto.

According to the present disclosure, the material used for the second layer of the alloy composite nanostructure is composed of a material having a higher surface energy than the metal used for the first layer, and dielectric deposition through thermal evaporation, and the second layer may be formed by dielectric deposition using a thermal deposition technique, self-assembly monolayer coating, or TEOS coating, without being limited thereto.

According to the present disclosure, the type of material used as the substrate of the alloy composite nanostructure including the first layer and the second layer is at least one selected from the group consisting of silicon, silicon oxide, silicon nitride, paper, and fiber, without being limited thereto. Surface energy and SERS enhancement factor may be optimized by adjusting the thicknesses of individual materials used for the first and second layers, depending on the size, emission speed, emission angle, or emission amount of respiratory droplets to be trapped.

When the composite nanostructure-based SERS chip is attached to a dental mask and a KF mask, it may continuously trap respiratory droplets, and it may be used for diagnosis of various diseases by analyzing the SERS signal of biomarkers present in the trapped respiratory droplets.

According to the present disclosure, the Raman and SERS signals obtained through examples may be subjected to in-depth analysis using machine learning-based software, and the machine learning algorithm may be a learning algorithm including one or more selected from the group consisting of autoencoding, logistic regression, principal component analysis, and a confusion matrix. Through the algorithm of the present disclosure, it is possible to identify components in respiratory droplets at concentrations lower than a general detection limit. Specifically, it is possible to identify two or more multiple target constituents through the machine learning algorithm.

The features and advantages of the present disclosure are summarized as follows.

The present disclosure provides a fine particle-trapping sensor including: a plasmonic hotspot layer formed of a first metal; and a trapping layer formed of a second material.

The inventors of the present disclosure have made extensive research efforts to develop a more effective and novel sensor for the real-time and high-sensitivity detection of droplets emitted from the oral cavity. As a result, the present inventors have developed an alloy composite nanostructure including a Raman sensor layer, formed of a metal, and a trapping layer formed of a dielectric material, and have found that, when the ratio between the two layers is adjusted, the alloy composite nanostructure effectively traps respiratory droplets rapidly emitted from the oral cavity and detects coronavirus (SARS-CoV-2 lysate) in the respiratory droplets at a concentration of 10 pfu/ml, indicating that the alloy composite nanostructure may be very advantageously used in the field of fine particle trapping.

BRIEF DESCRIPTION OF THE DRAWINGS

FIG. 4 shows a droplet detection experiment conducted using the enhanced surface energy of the gold-titanium oxide composite nanostructure, according to one experimental example of the present disclosure.

DETAILED DESCRIPTION

Hereinafter, the present disclosure will be described in more detail with reference to examples. These examples are only for illustrating the present disclosure in more detail, and it will be apparent to those of ordinary skill in the art that the scope of the present disclosure according to the subject matter of the present disclosure is not limited by these examples.

EXAMPLES

Fabrication of Alloy Composite Nanostructures

Figure 1:
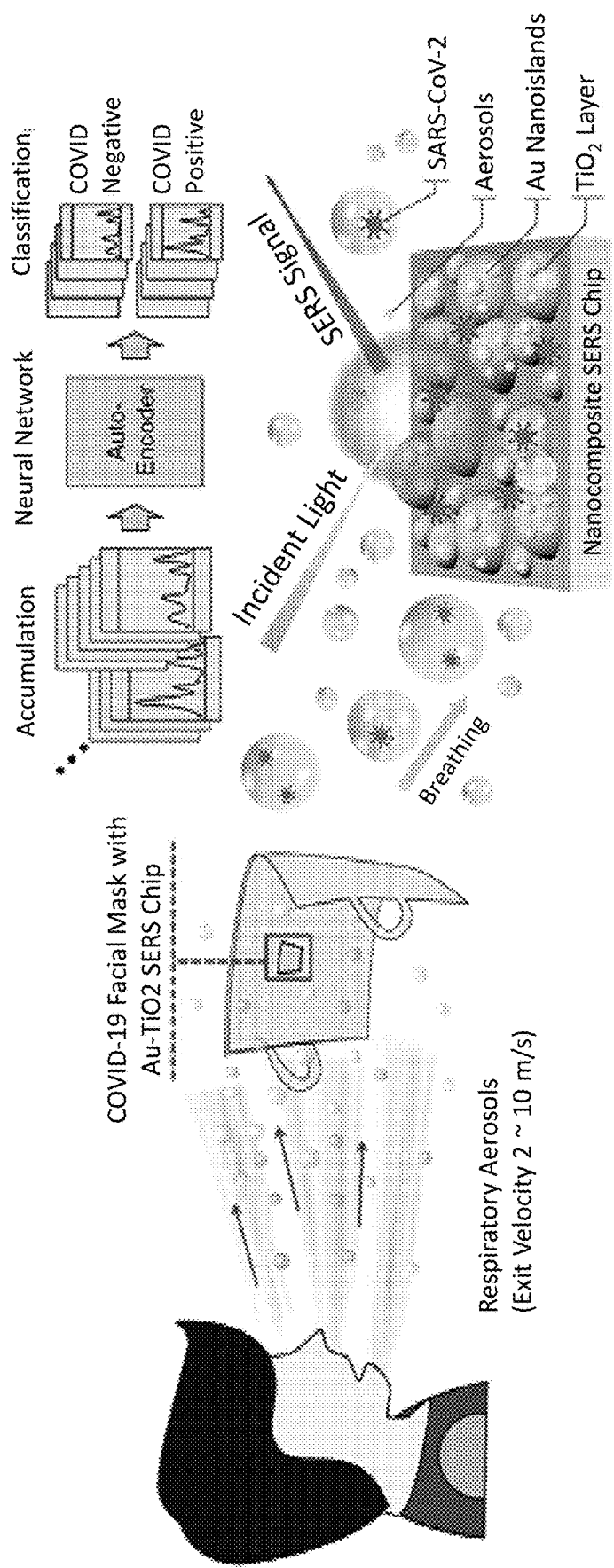
FIG. 1 shows a gold-titanium dioxide composite nanostructure fabricated according to one embodiment of the present disclosure, and shows that the composite nanostructure detects the spike protein of coronavirus (SARS-CoV-2) in respiratory droplets at a level of 100 pM, and that the concentration of coronavirus lysate is detected through a machine learning technique.
Figure 2:
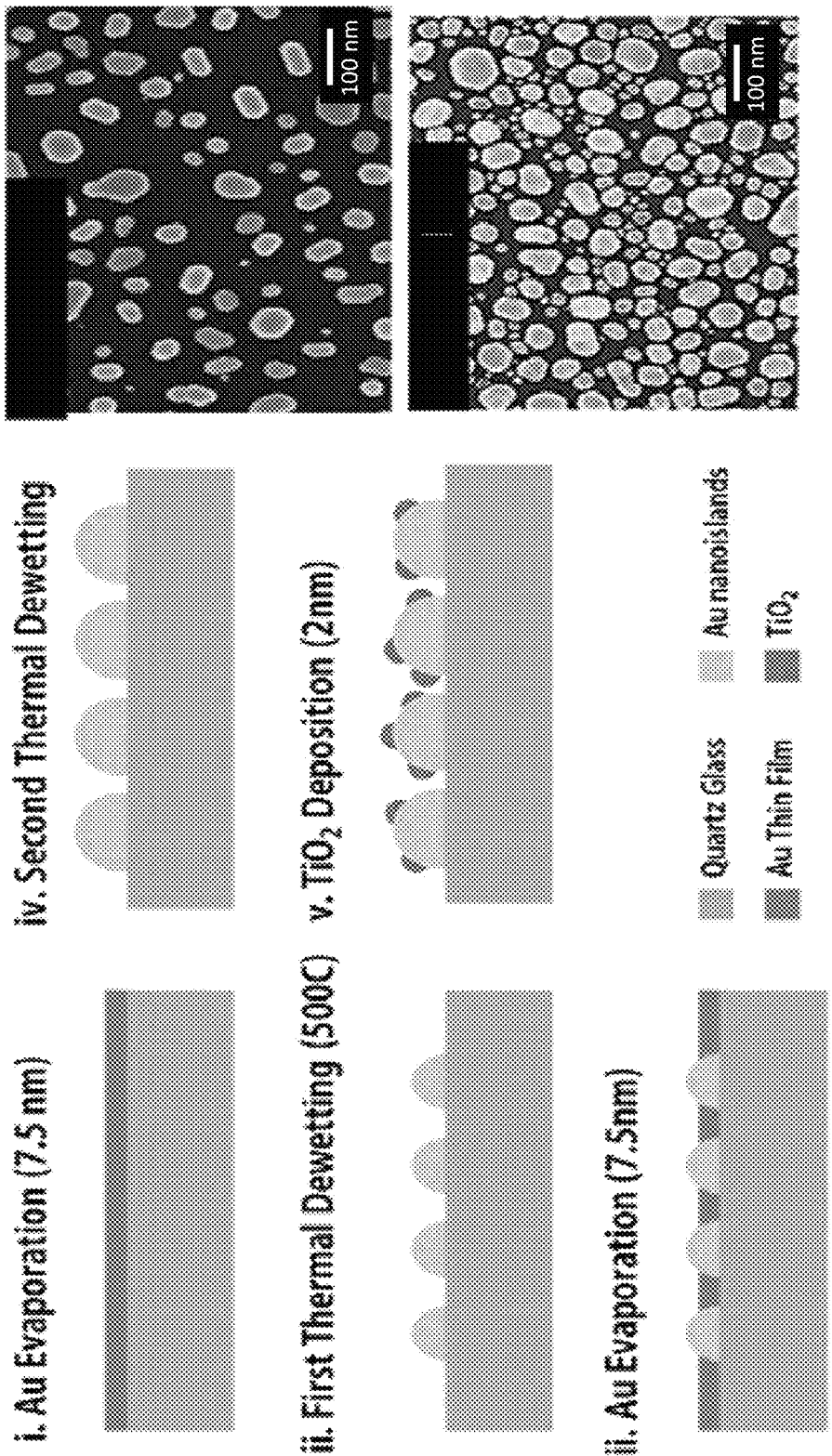
FIG. 2 shows the results of fabricating gold nanoisland structures as a first layer of an alloy composite nanostructure and depositing titanium dioxide as a second layer, according to one experimental example of the present disclosure.

In an example of the present disclosure, gold-titanium dioxide composite nanostructures were fabricated, and the spike protein of coronavirus (SARS-CoV-2) in respiratory droplets was detected at a level of 100 pM. In addition, a coronavirus lysate was successfully detected at a concentration of $10^1$ to $10^4$ pfu/ml through a machine learning technique (FIG. 1). As a first layer of the alloy composite nanostructure, gold nanoisland structures were fabricated, and as a second layer, titanium dioxide was deposited. The gold nanoisland structures were formed by heat-treating a 7.5-nm-thick gold thin film at a high temperature of 500° C., and the heat-treatment process was repeated once more to form nanostructures having high packing density and many plasmonic hotspots (FIG. 2).

Figure 3:
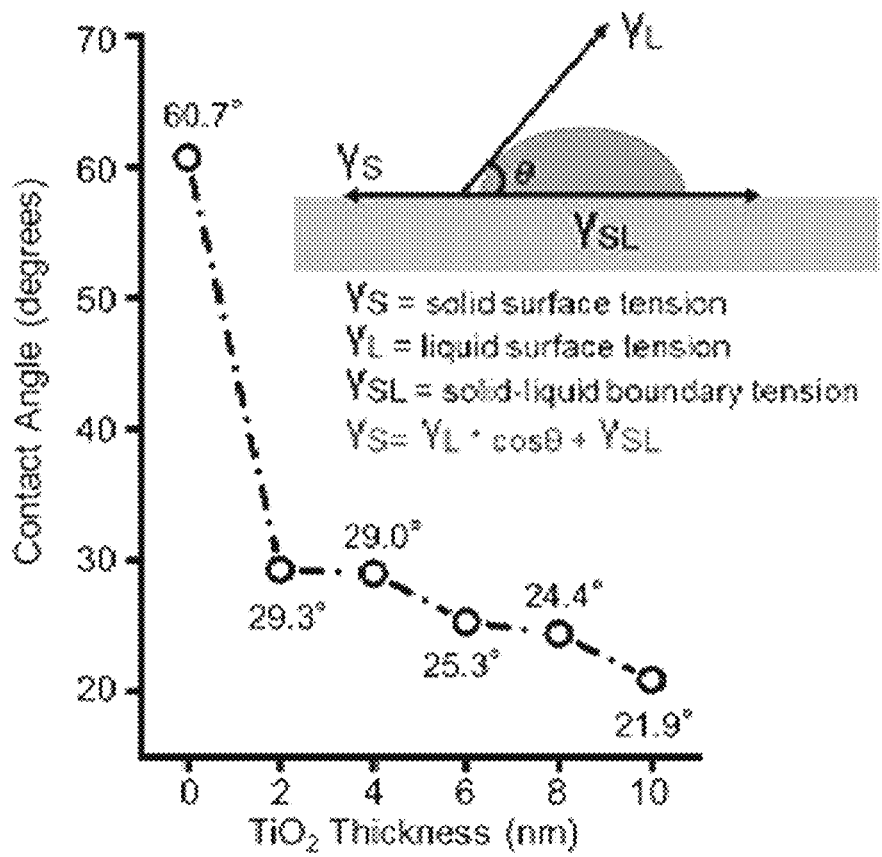
FIG. 3 shows an experiment conducted to measure a contact angle depending on the thickness of titanium dioxide in order to check whether the surface energy of the alloy composite nanostructure has been controlled, according to one experimental example of the present disclosure.
Figure 3:
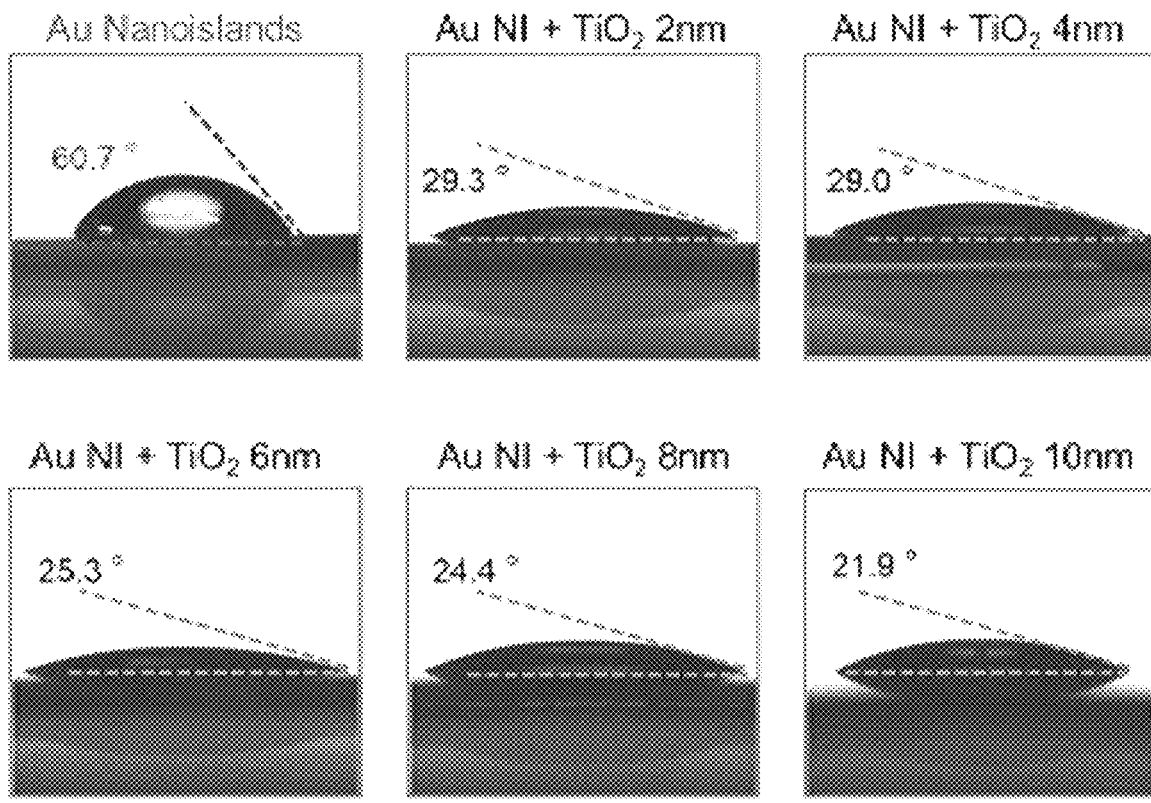

In order to check whether the surface energy of the alloy composite nanostructure was controlled, an experiment was conducted to measure the contact angle depending on the thickness of titanium dioxide. Contact angle measurement is a measurement technique that may indirectly determine the surface energy of the substrate, and higher contact angle indicates lower surface energy. It could be confirmed that, in the case of the gold nanoislands without titanium dioxide, the initial contact angle was very high) (60°), but when titanium dioxide was deposited to a thickness of 2 nm, the surface energy rapidly increased, and thus the contact angle decreased to 29.3°. It was confirmed that, when titanium dioxide was deposited to a thickness greater than 2 nm, the contact angle tended to decrease, but the degree of decrease in the contact angle was insignificant compared to the case of the initial 2-nm thickness (FIG. 3).

Droplet Detection Experiment

A droplet detection experiment was conducted using the enhanced surface energy of the gold-titanium dioxide composite nanostructure. To simulate respiratory droplets generated in the human body, droplets were sprayed onto the composite nanostructure substrate through a nebulizer. In this case, the size of the droplets formed was 10 µm or less in diameter.

In order to verify the enhancement of droplet adsorption ability caused by the increase in the surface energy, rhodamine 6G (R6G) molecules at a concentration of 100 nM were sprayed in the form of droplets through a nebulizer, and the SERS signal was measured depending on the thickness of titanium dioxide. Rhodamine 6G is a sample frequently used as a reference molecule in the measurement of SERS signals. In measurement of the SERS signal, the acquisition time was 1 second, and the nebulizing time was 10 seconds. As a result of the experiment, it was confirmed that the previously reported specific SERS signals of R6G appeared at 773, 1,183, 1,360, and 1,507 $cm^{-1}$ appeared, and the signal at 1360 $cm^{-1}$ was quantified depending on the titanium oxide thickness (0 nm to 10 nm).

Figure 4:
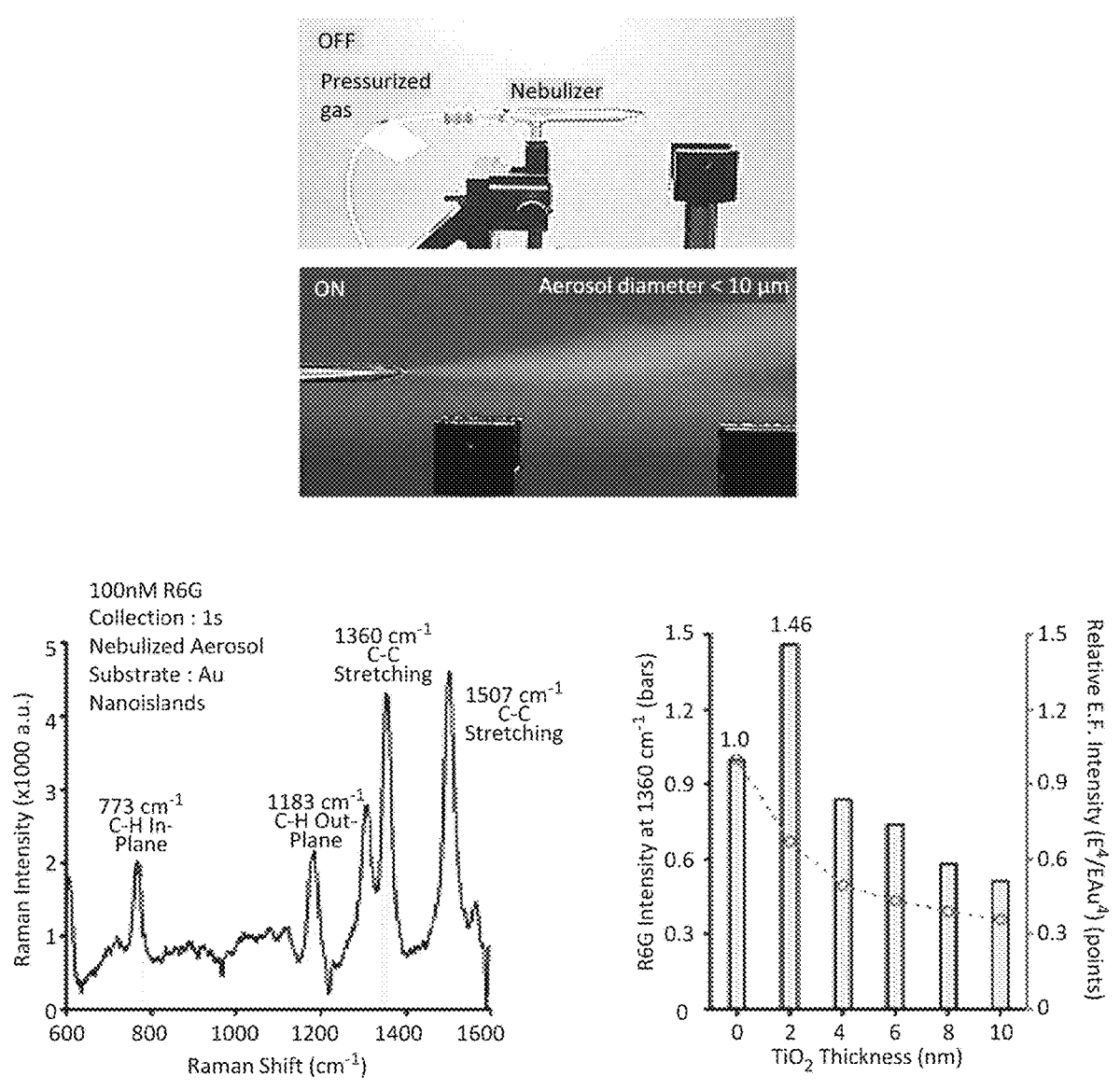

The graph at the right-hand axis on the bottom right of FIG. 4 shows the results of quantifying electric field enhancement occurring on the local surface of the nanostructure depending on the thickness of titanium dioxide calculated through the finite element time domain (FDTD) technique.

In general, when a dielectric such as titanium dioxide is deposited on a metal surface, the E-field intensity decreases in proportion to the distance. Thus, as the thickness of titanium dioxide increases, the E-field intensity decreases, and for this reason, the intensity of the plasmonic hotspots decreases, and ultimately, the intensity of the SERS signal also decreases. However, from the results of this experiment, it was confirmed that, despite the decrease in the E-field intensity due to the deposition of titanium oxide, a larger number of R6G droplets were trapped on the same substrate area due to the high surface energy, and when titanium dioxide was deposited to a thickness of 2 nm, the SERS signal was enhanced by 1.46 times compared to the signal acquired using the existing gold nanoislands.

Analysis of SERS Signal of R6G

Figure 5:
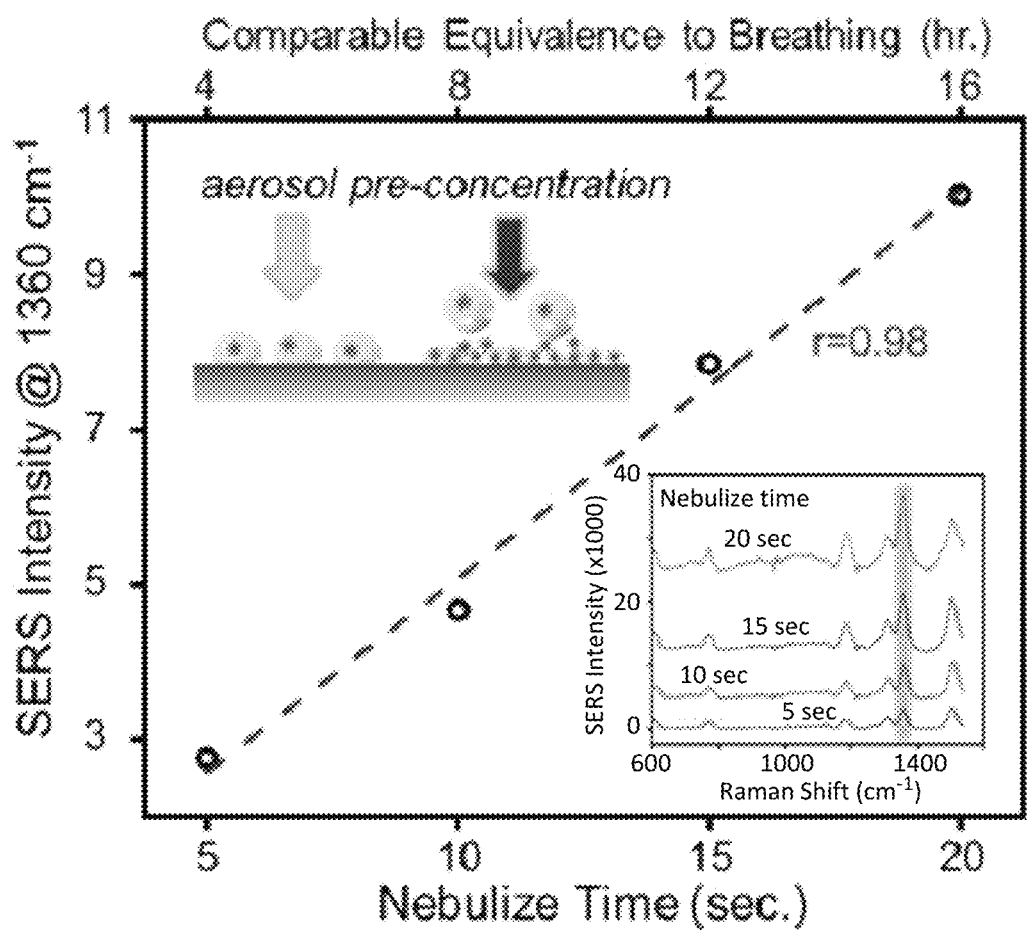
FIG. 5 shows the results of quantifying the SERS signal of rhodamine 6G (R6G) depending on the nebulizing time, according to one experimental example of the present disclosure.

The SERS signal of R6G was quantified depending on the nebulizing time, and it can be seen that the SERS signal at 1360 $cm^{-1}$ increases linearly as the nebulizing time increased to 5, 10, 15, or 20 seconds. Thereby, it is expected that, when the composite nanostructure is attached to a mask, it may continuously trap respiratory droplets, and when the mask is worn for a long period of time, it is possible to cumulatively trap a low volume of respiratory droplets. The number of droplets sprayed through a nebulizer for 5 seconds is the same as the number of droplets emitted during breathing for about 4 hours on average (FIG. 5).

Figure 6:
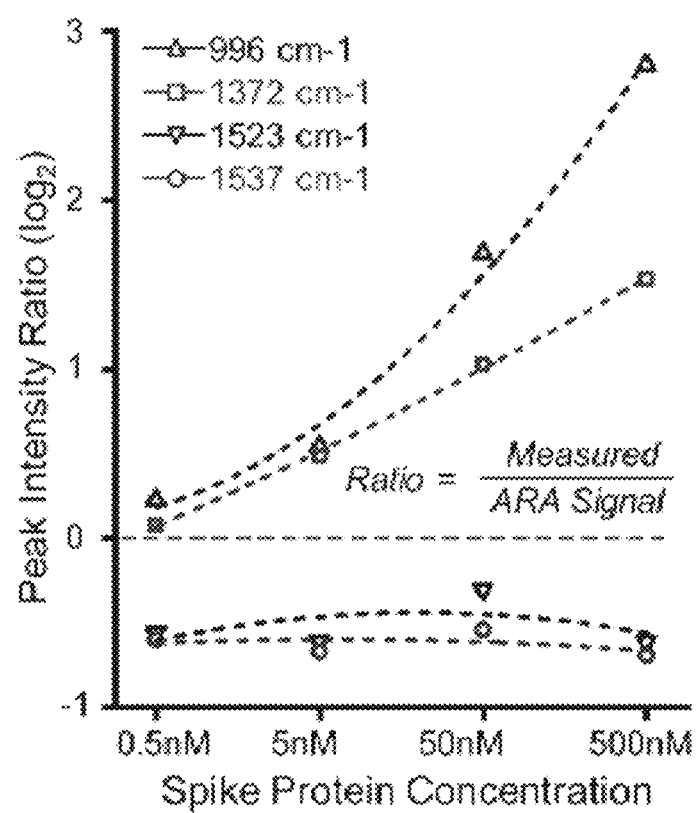
FIG. 6 shows the results of preparing artificial respiratory aerosol (ARA) to simulate respiratory droplets of coronavirus patients, adding SARS-CoV-2 spike protein to the artificial respiratory aerosol (ARA) at a concentration of 100 pM to 100 nM, and spraying the mixture in the form of droplets, according to one experimental example of the present disclosure.

Artificial respiratory aerosol (ARA) was prepared to simulate respiratory droplets of coronavirus patients, and 100 pM to 100 nM of SARS-CoV-2 spike protein was added thereto at various concentrations and sprayed in the form of droplets (FIG. 6). The spike protein is a protein distributed on the surface of coronavirus, and corona virus infection may be determined by detection of this protein. The table below shows the constituents and concentrations used in the preparation of the artificial respiratory droplets, and shows the SERS peaks observed depending on the constituents and concentrations. Underlining denotes non-discriminatory SERS peaks.

| Constituent | Concentration | SERS Peaks (cm$^{-1}$) |
|---|---|---|
| Sodium Chloride | 27.3 μM | 723 |
| Ammonium Nitrate | 4.1 μM | 1057 |
| Potassium Phosphate | 4.6 μM | 1003, 1585 |
| Potassium Chloride | 1.6 μM | 1063, 1523, 1573 |
| Potassium Citrate | 1.0 μM | 1003, 1280, 1582 |
| Uric Acid | 100 nM | 648, 756, 1342, 1581 |
| Urea | 3.3 μM | 1007, 1620 |
| Lactic Acid | 1.2 μM | 866, 1574 |
| Spike Protein | <1 μM | 996, 1372, 1523, 1537 |

In particular, it was confirmed that, in the case of the spike protein, a total of four specific peaks were observed, and thereamong, the signals at peaks of 1,523 and 1,537 cm$^{-1}$ were somewhat similar to the signals of the preceding ARA constituents.

Results of Detection of Coronavirus Lysate by Complex Nanostructures

FIG. 6 shows the results of tracking the four peaks of the spike protein depending on the spike protein concentration. Similar to the previous results, it was confirmed that the signals at 1,523 and 1,537 cm$^{-1}$ showed constant values regardless of the concentration due to the signal generated in ARA, but the signals at 996 and 1,372 cm$^{-1}$ increased as the concentration of the spike protein increased. In this case, the signals at 1,523 and 1,537 cm$^{-1}$ were named non-discriminatory SERS peaks, and the signals at 996 and 1,372 cm$^{-1}$ were named highly discriminatory peaks.

Figure 7:
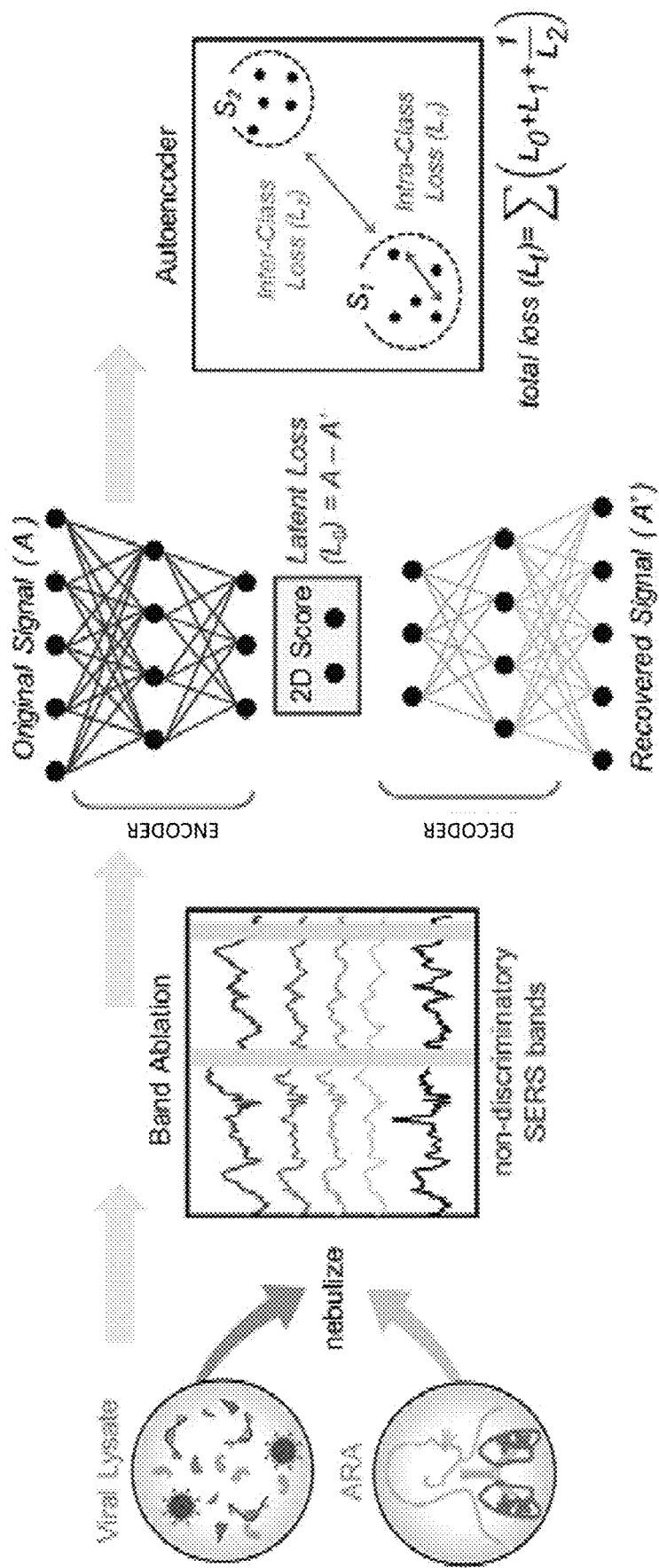
FIG. 7 shows a result of detecting a coronavirus lysate by the composite nanostructure, according to one experimental example of the present disclosure.

Finally, it was confirmed that the coronavirus lysate was detected by the composite nanostructures of the present disclosure (FIG. 7). Unlike a purified spike protein, the lysate of the virus generates complex signals such as RNA, membrane, etc., and thus the concentration gradient through only a simple SERS signal has a limitation. Therefore, in this experiment, the acquired SERS signal was learned using a neural network-based autoencoder algorithm, and an algorithm capable of distinguishing the SERS signal depending on the virus concentration was designed.

Machine Learning by Autoencoder Algorithm

A lysate was added to ARA at various concentrations ($10^1$ to $10^4$ pfu/ml) and sprayed on the composite nanostructures in the form of droplets, and the SERS signals were acquired. Thereafter, in order to increase the learning efficiency, the non-discriminatory SERS peaks shown in FIG. 6 were excluded through an ablation process. Next, the corresponding SERS signals were input to the encoding stage of the autoencoder and divided into two main features (2D scores), and then the SERS signals recovered through a decoding process were acquired. The two features were represented by the x and y axes on the latent space, and the SERS signals at the same concentration were clustered.

Figure 8:
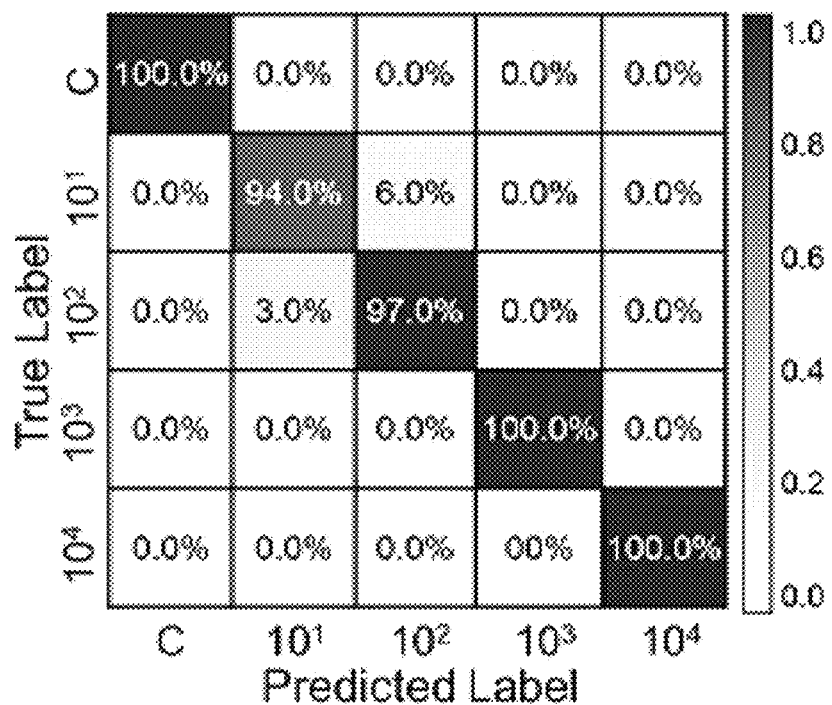
FIG. 8 shows the distribution of SERS signals of a coronavirus lysate learned through an autoencoder algorithm, according to one experimental example of the present disclosure.
Figure 8:
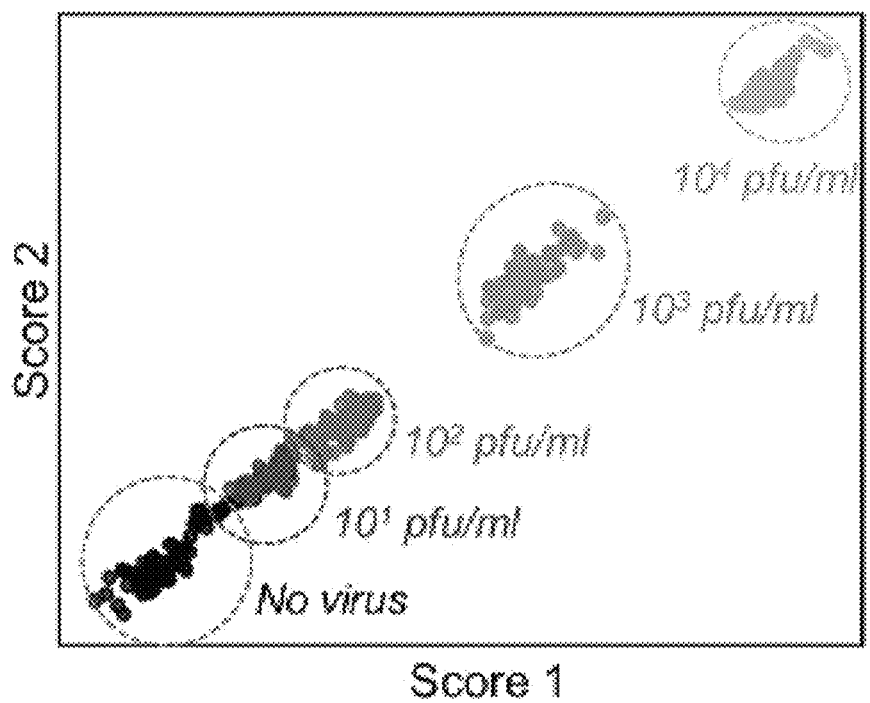

In the above-described process, a total of three losses occurred: 1) a latent loss that is the difference between the original SERS signal and the recovered SERS signal; 2) an intra-class loss occurring in the cluster at the same concentration; and 3) an inter-class loss occurring in the clusters at different concentrations. This autoencoder algorithm was learned in a way to minimize the three losses, and FIG. 8 shows the distribution of the SERS signal of the coronavirus lysate learned through the autoencoder algorithm.

As a result of the learning, it can be seen that the lysate at a concentration of $10^1$ to $10^4$ pfu/ml clearly formed a cluster, and it was confirmed that the SERS signal was linearly distributed on the 2D latent space depending on the lysate concentration. The right side of FIG. 8 is a confusion matrix indicating the accuracy of the present model, and is an index indicating how accurately the SERS signal input to this model may distinguish the lysate concentration. For example, when a signal corresponding to a concentration of $10^1$ pfu/ml is input to this algorithm, it distinguishes $10^1$ pfu/ml with 94% accuracy, but it is recognized as a signal corresponding to $10^2$ pfu/ml with a 6% error.

Finally, it was confirmed that the SARS-CoV-2 lysate at a concentration of $10^1$ to $10^4$ pfu/ml was distinguished with an accuracy of 98% or more by using this autoencoder model and the composite nanostructure SERS substrate.

Although the present disclosure has been described in detail with reference to the specific features, it will be apparent to those skilled in the art that this description is only of a preferred embodiment thereof, and does not limit the scope of the present disclosure. Thus, the substantial scope of the present disclosure will be defined by the appended claims and equivalents thereto.

What is claimed is:

1. A fine particle trapping sensor for trapping fine particles, the sensor comprising:
    a plasmonic hotspot layer formed of a first metal, wherein the plasmonic hotspot layer comprises nanoisland structures; and
    a trapping layer formed of a second material, wherein the trapping layer is deposited on a surface of the plasmonic hotspot layer.

2. The sensor according to claim 1, which is an alloy composite nanostructure.

3. The sensor according to claim 1, which is capable of continuously trapping the fine particles.

4. The sensor according to claim 2, which is capable of binding to any one or more materials selected from a group consisting of silicone, silicon oxide, silicon nitride, paper, and fiber.

5. The sensor according to claim 1, wherein the first metal is any one or an alloy of two or more selected from a group consisting of gold (Au), silver (Ag), copper (Cu), aluminum (Al), lead (Pb), and palladium (Pd).

6. The sensor according to claim 1, wherein the second material is any one or an alloy of two or more selected from a group consisting of titanium dioxide ($TiO_2$), zinc oxide (ZnO), nickel oxide (NiO), and stannous oxide (SnO).

7. The sensor according to claim 6, wherein the trapping layer is formed by depositing the second material on the surface of the plasmonic hotspot layer, followed by a self-assembled monolayer coating.

8. The sensor according to claim 1, wherein the second material has a higher surface energy than the first metal.

9. The sensor according to claim 1, wherein the trapping layer is located in a cluster form on the surface of the plasmonic hotspot layer.

10. The sensor according to claim 1, wherein the fine particle is a particulate matter, pollen, fungus, heavy metal, or droplet.

11. A method for component analysis of fine particles, the method comprising-steps of:
    (a) trapping the fine particles by the sensor according to claim 1;

(b) measuring surface-enhanced Raman spectroscopy (SERS) signals from the trapped fine particles;
(c) analyzing the SERS signals by a machine learning-based algorithm; and
(d) determining a concentration of a component of the trapped fine particles based on the analysis of the SERS signals.

12. The method according to claim 11, wherein the algorithm is one or more selected from a group consisting of autoencoding, logistic regression, principal component analysis, and confusion matrix.

13. The method according to claim 12, wherein the algorithm is capable of identifying multiple target constituents.

14. The method according to claim 12, wherein the fine particle is a particulate matter, pollen, fungus, heavy metal, or droplet.

15. The method according to claim 11, wherein the component of the trapped fine particles is a lysate of SARS-CoV-2.

16. The method according to claim 1, wherein each of the nanoisland structures has a size in the range of 20 to 200 nm.

17. A method for fabricating a sensor for trapping fine particles, the method comprising steps of:
(a) forming a plasmonic hotspot layer of a first metal, wherein the plasmonic hotspot layer comprises nanoisland structures; and
(b) forming a trapping layer of a second material, wherein the trapping layer is deposited on a surface of the plasmonic hotspot layer.

18. The method according to claim 17, wherein the first metal in step (a) is any one or an alloy of two or more selected from a group consisting of gold (Au), silver (Ag), copper (Cu), aluminum (Al), lead (Pd), and palladium (Pd).

19. The method according to claim 17, wherein the second material in step (b) is any one or an alloy of two or more selected from a group consisting of titanium dioxide ($TiO_2$), zinc oxide (ZnO), nickel oxide (NiO), and stannous oxide (SnO).

20. The method according to claim 17, further comprising determining a surface energy of the trapping layer by contact angle measurement.

* * * * *